(12) United States Patent
Gaier et al.

(10) Patent No.: US 11,826,098 B2
(45) Date of Patent: Nov. 28, 2023

(54) SYSTEM AND METHOD FOR THE TREATMENT OF AMBLYOPIA

(71) Applicant: Massachusetts Eye and Ear Infirmary, Boston, MA (US)

(72) Inventors: Eric Gaier, Boston, MA (US); Dean Travers, Cambridge, MA (US); Scott Xiao, Cambridge, MA (US)

(73) Assignee: Massachusetts Eye and Ear Infirmary, Boston, MA (US)

(*) Notice: Subject to any disclaimer, the term of this patent is extended or adjusted under 35 U.S.C. 154(b) by 157 days.

(21) Appl. No.: 16/345,632

(22) PCT Filed: Nov. 2, 2017

(86) PCT No.: PCT/US2017/059775
§ 371 (c)(1),
(2) Date: Apr. 26, 2019

(87) PCT Pub. No.: WO2018/085576
PCT Pub. Date: May 11, 2018

(65) Prior Publication Data
US 2020/0054205 A1 Feb. 20, 2020

Related U.S. Application Data

(60) Provisional application No. 62/448,479, filed on Jan. 20, 2017, provisional application No. 62/416,355, filed on Nov. 2, 2016.

(51) Int. Cl.
*A61B 3/028* (2006.01)
*A61B 3/00* (2006.01)
*G02B 27/00* (2006.01)

(52) U.S. Cl.
CPC ............ *A61B 3/028* (2013.01); *A61B 3/0058* (2013.01); *G02B 27/005* (2013.01)

(58) Field of Classification Search
CPC ......... A61B 3/00; A61B 3/0058; A61B 3/005; A61B 3/0041; A61B 3/02; A61B 3/028;
(Continued)

(56) References Cited

U.S. PATENT DOCUMENTS

2012/0127426 A1  5/2012  Backus et al.
2016/0270656 A1  9/2016  Samec et al.
(Continued)

FOREIGN PATENT DOCUMENTS

CN        103239347 A  *  8/2013
WO    WO 2015/145111      10/2015

OTHER PUBLICATIONS

English Machine translation of Pu et al. CN-103239347-A (Year: 2013).*
(Continued)

*Primary Examiner* — Marin Pichler
(74) *Attorney, Agent, or Firm* — Fish & Richardson P.C.

(57) ABSTRACT

A system and methods for the treatment of amblyopia are described. The system includes a display system capable of in delivering a second image to a second eye of a patient and a first image to a first eye of a patient. The system also includes a controller in capable of delaying the delivery of the second image to the second eye of the patent. The controller is configured to receive the second image and the first image. The controller is also configured to identify a delay factor associated with the second image. The controller is also configured to provide the first image to the display system for viewing by the first eye of the patient. The controller is also configured such that after a delay determined by the delay factor, the controller provides the second image to the display system for viewing by the second eye of the patient.

12 Claims, 6 Drawing Sheets

(58) Field of Classification Search
CPC .. A61B 3/08; A61B 3/085; A61B 3/10; A61B 3/12; A61B 3/103; A61B 3/102; A61B 3/14; A61H 5/00; A61H 5/005; A61F 9/008
USPC .......................................................... 351/203
See application file for complete search history.

(56) References Cited

U.S. PATENT DOCUMENTS

| | | | | |
|---|---|---|---|---|
| 2017/0000326 | A1* | 1/2017 | Samec | A61B 3/1216 |
| 2018/0132751 | A1* | 5/2018 | Yarden | A61H 5/00 |
| 2018/0136486 | A1* | 5/2018 | Macnamara | G02C 11/10 |
| 2018/0168444 | A1* | 6/2018 | Foss | A61B 3/08 |
| 2020/0329961 | A1* | 10/2020 | Oz | A61B 3/00 |

OTHER PUBLICATIONS

Donaghy et al, "Vision screening for amblyopia," EyeRounds.org, Aug. 11, 2015, 11 pages.
Hess et al., "Amblyopia and the binocular approach to its therapy," Vision Research, Sep. 1, 2015, 114:4-16.
PCT International Preliminary Report on Patentability for International Appln. No. PCT/US2017/059775, dated May 7, 2019, 7 pages.
PCT International Search Report in International Appln. No. PCT/US2017/059775, dated Jan. 25. 2018, 12 pages.
Bi et al., "Neuronal Responses in Visual Area V2 (V2) of Macaque Monkeys with Strabismic Amblyopia," Cereb Cortex., Sep. 2011, 21(9):2033-45.
Birch and Kelly, "Amblyopia and the whole child," Prog Retin Eye Res., Mar. 2023, 93:101168, 20 pages.
Birch et al., "Abstract: The Role of Interocular Suppression in the Etiology of Amblyopia and its Response to Treatment," Abstract, Presented at Proceedings of the 2017 ARVO Annual Meeting, Baltimore, MD, May 7-11, 2017; 58(8): 1 page.
Birch et al., "Assessing Suppression in Amblyopic Children With a Dichoptic Eye Chart," Invest Ophthalmol Vis Sci., Oct. 2016, 57(13):5649-5654.
Birch et al., "Binocular amblyopia treatment with contrast-rebalanced movies," J AAPOS, Jun. 2019, 23(3):160.e1-160.e5.
Birch et al., "Binocular iPad treatment for amblyopia in preschool children," J AAPOS, Feb. 2015, 19(1):6-11.
Birch et al., "Dichoptic and Monocular Visual Acuity in Amblyopia," Am J Ophthalmol., Oct. 2022, 242:209-214.
Birch, "Amblyopia and binocular vision," Prog Retin Eye Res., Mar. 2013, 33:67-84.
Cooke and Bear, "How the mechanisms of long-term synaptic potentiation and depression serve experience-dependent plasticity in primary visual cortex," Philosophical Transactions of The Royal Society B Biological Sciences, Apr. 2014, 369(1639):20140021, 2 pages.
Feldman, "The Spike-Timing Dependence of Plasticity," Neuron, Aug. 2012, 75(4):556-71.
Fu et al., "Temporal Specificity in the Cortical Plasticity of Visual Space Representation," Science, Jun. 2002, 296(5575):1999-2003.
Gambacorta et al., "An action video game for the treatment of amblyopia in children: A feasibility study," Vision Res., Jul. 2018, 148:1-14.
Heynen et al., "Molecular mechanism for loss of visual cortical responsiveness following brief monocular deprivation," Nat Neurosci., Aug. 2003, 6(8):854-62.
Huang et al., "Associative Hebbian Synaptic Plasticity in Primate Visual Cortex," Journal of Neuroscience, May 2014, 34(22):7575-7579.
Jost et al., "A randomized clinical trial of contrast increment protocols for binocular amblyopia treatment," J AAPOS., Oct. 2020, 24(5):282.e1-282.e7.
Jost et al., "Randomized clinical trial of streaming dichoptic movies versus patching for treatment of amblyopia in children aged 3 to 7 years," Sci Rep., Mar. 2022, 12(1):4157, 9 pages.
Kelly et al., "Binocular iPad Game vs Patching for Treatment of Amblyopia in Children A Randomized Clinical Trial," JAMA Ophthalmol., Dec. 2016, 134(12):1402-1408.
Li et al., "Dichoptic movie viewing treats childhood amblyopia," Journal of American Association for Pediatric Ophthalmology and Strabismus, Oct. 2015, 19(5):401-405.
Manny et al., "A Randomized Trial of Binocular Dig Rush Game Treatment for Amblyopia in Children Aged 4 to 6 Years of Age," Optom. Vis. Sci., Mar. 2022, 99(3):213-227, 42 pages.
McMahon and Leopold, "Stimulus Timing-Dependent Plasticity in High-Level Vision," Curr Biol., Feb. 2012, 22(4):332-7.
Sengpiel and Vorobyov, "Intracortical Origins of Interocular Suppression in the Visual Cortex," J Neurosci., Jul. 2005, 25(27):6394-400.
Smith et al., "Bidirectional synaptic mechanisms of ocular dominance plasticity in visual cortex," Philos Trans R Soc Lond B Biol Sci., Feb. 2009, 364(1515):357-67.
Tao et al., "Early Monocular Defocus Disrupts the Normal Development of Receptive-Field Structure in V2 Neurons of Macaque Monkey," J Neurosci., Oct. 2014, 34(41): 13840-13854.
Vedamurthy et al., "A dichoptic custom-made action video game as a treatment for adult amblyopia," Vision Res., Sep. 2015, 114:173-87.
Xiao et al., "Randomized Controlled Trial of a Dichoptic Digital Therapeutic for Amblyopia," Ophthalmology, Jan. 2022, 129(1):77-85.
Yao and Dan, "Stimulus Timing-Dependent Plasticity in Cortical Processing of Orientation," Neuron, Oct. 2001, 32(2):315-23.

* cited by examiner

SYSTEM AND METHOD FOR THE TREATMENT OF AMBLYOPIA

CLAIM OF PRIORITY

This application is a 371 U.S. National Application of PCT/US2017/059775, filed on Nov. 2, 2017, which claims priority under to U.S. Patent Application Ser. No. 62/448,479, filed on Jan. 20, 2017, and U.S. Patent Application Ser. No. 62/416,355, filed on Nov. 2, 2016. The entire contents of the foregoing are hereby incorporated by reference.

BACKGROUND

Amblyopia (commonly referred to as "lazy eye") is a condition characterized by reduced vision in a structurally normal eye that results from maldevelopment of the visual system secondary to an abnormal binocular visual experience during infancy or early childhood.

Virtual reality headsets and 3D televisions create the percept of three dimensional space by presenting a slightly spatially different image to each eye. In general, the brain interprets the left-eye and right-eye views of the same scene as a single three-dimensional image (referred to as a stereoscopic image).

SUMMARY

This specification describes technologies relating to the treatment of amblyopia.

In general, one innovative aspect of the subject matter described in this specification can be embodied in a system that includes a display system capable of delivering a second image to a second eye of a patient and a first image to a first eye of a patient. The system also includes a controller capable of delaying the delivery of the second image to the second eye of the patient. The controller is configured to receive the second image and the first image. The controller is also configured to identify a delay factor associated with the second image. The controller is also configured to provide the first image to the display system for viewing by the first eye of the patient. The controller is also configured such that after a delay determined by the delay factor, the controller provides the second image to the display system for viewing by the second eye of the patient.

The methods may include one or more of the following features, alone or in combination. The delay factor may be between 0 to 1000 milliseconds. The first image and the second image may be presented through a single display and selectively filtered to each eye. The display system may use polarization to selectively deliver the first image and the second image. The first image and the second image may be presented through separate displays or a single split display presented or projected to each eye. The first image and the second image may be part of a virtual reality experience. The first image and the second image may be part of an augmented reality experience. The delay factor may be determined at least in part by electrophysiologic measures including from VEPs and/or EEG recordings, by other visual measurements or tests, such as but not limited to eye tracking technologies, game-based tests of binocularity or inter-ocular suppression.

Other implementations of any of the above aspects include corresponding systems, apparatus, and computer programs that are configured to perform the actions of the methods, encoded on computer storage devices. The present disclosure also provides a computer-readable storage medium coupled to one or more processors and having instructions stored thereon which, when executed by the one or more processors, cause the one or more processors to perform operations in accordance with implementations of the methods provided herein. The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

Particular embodiments of the subject matter described in this specification can be implemented so as to realize one or more of the following advantages.

The details of one or more embodiments of the subject matter described in this specification are set forth in the accompanying drawings and the description below. Other features, aspects, and advantages of the subject matter can become apparent from the description, the drawings, and the claims.

BRIEF DESCRIPTION OF THE DRAWINGS

Like reference numbers and designations in the various drawings indicate like elements.

DETAILED DESCRIPTION

The mammalian visual cortex integrates signals from each eye and abides by basic principles of neural and synaptic plasticity. Plasticity, occurring at a single synapse, can in turn rewire neural circuits and change signal processing and integration within the nervous system; as such, synaptic plasticity is widely accepted as neurophysiologic model and mechanism for learning and memory. Decades of work in the mammalian brain has detailed the strong timing-dependence of integrated neural signals that influences the direction of synaptic plasticity as potentiation or depression. Amblyopia is a neurodevelopmental disease characterized by impairment in monocular vision that results from abnormal visual experience during visual development.

Figure 1:
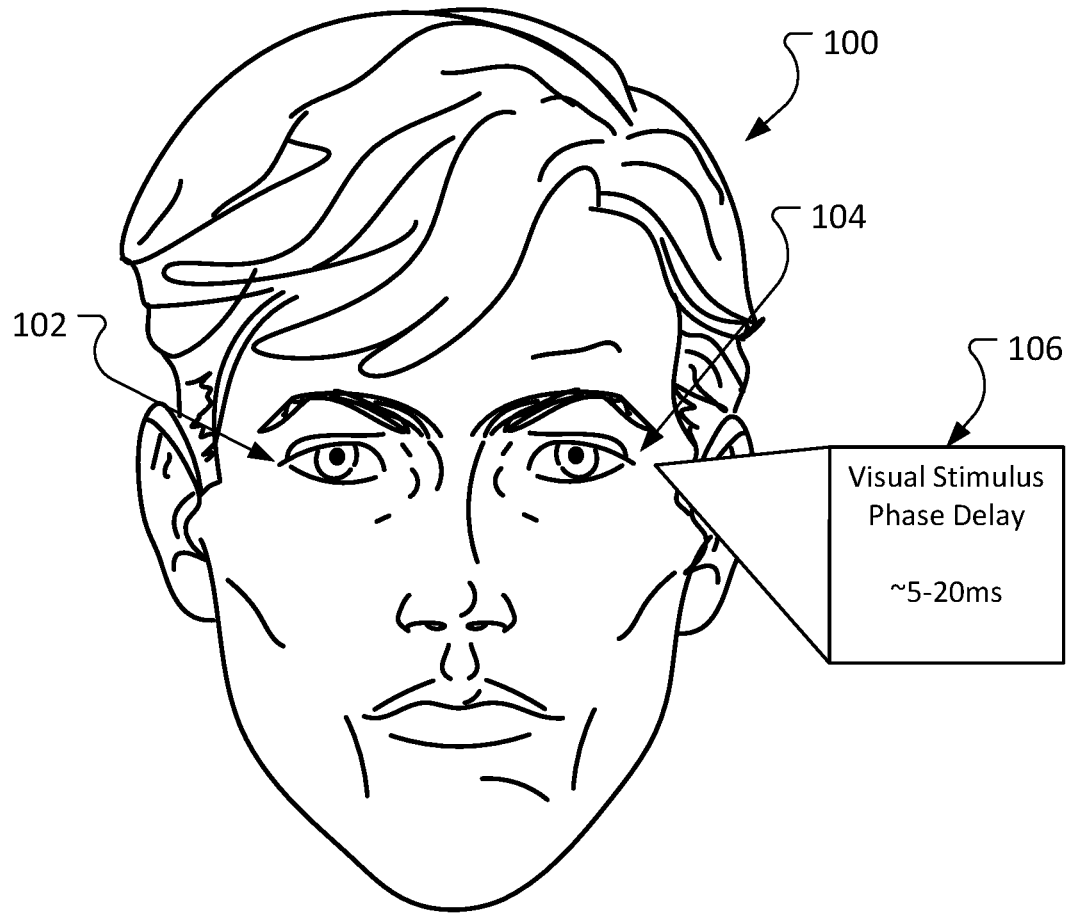
FIG. 1 illustrates a human face.

FIG. 1 illustrates a human face. An individual 100 with amblyopia has a neurological disorder in which the visual input from one eye 102 (referred to herein as the preferred eye 102) dominates activation of the visual cortex over the other eye 104 (referred to herein as the affected eye 104). Amblyopia is one example in which visual experience and signal processing in the visual system influences the wiring of the visual system through synaptic plasticity and abides by the same timing-dependent principles.

The capacity or tendency for plasticity, termed metaplasticity, changes during neurodevelopment and in general reduces going from childhood into adulthood. This phenomenon is also demonstrated in amblyopia in the sense that treatment, aimed at strengthening the weaker eye through altering the subject's visual experience via methods discussed below, becomes ineffective if implemented after a certain age. Even within this "critical window" of cortical synaptic plasticity, occlusion (patching) therapy has limited efficacy with a high rate of failure. The efficacy of occlusion therapy may represent release of a suppressive role of the preferred eye that otherwise prevents recovery of vision in the amblyopic eye. Reduction of contrast in the fellow eye has also been employed to balance the visual utility of the eyes to minimize suppression, but this approach has shown similar efficacy to patching. Reducing contrast in the preferred eye of amblyopic patients has an immediate effect of reducing suppression to promote use of the affected eye.

The visually evoked potential (VEP) is a powerful physiologic measure of vision in non-communicative patients and animal models of amblyopia. Visual cortical responses, measured by VEP, are delayed (prolonged implicit time) with stimulation of the affected eye of patients with amblyopia ranging by 5-20 ms. There is also a direct relationship between the degree of visual deficit and the visual stimulus phase delay 106. Patch therapy (covering the preferred eye with a patch) improves the delay in VEP signals initiated in the affected eye of some 2-6 year old patients.

The delayed VEP implicit time is considered as a biomarker for amblyopia, but this delay may instead represent a mechanism by which the preferred eye acts to preclude recovery of the affected eye. As described herein, amblyopia may be treated by altering the timing of presentation of images to the preferred eye and the affected eye in order to facilitate synaptic plasticity in the visual cortex with the goal of increasing visual cortical responsiveness, and in turn visual function, of the affected eye. The present disclosure thus provides methods of treating subjects with amblyopia by altering the timing of presentation of images to the preferred eye and the affected eye in order to cause the brain to process images from the affected eye, e.g., using the devices described herein. Amblyopia can be diagnosed using methods known in the art, including by assessing fixation preference or by using forced preferential looking tests such as Teller cards, optical tracking, detecting lack of optokinetic nystagmus in one eye, neutral density filter testing, or visual evoked potentials (VEP) testing. See, e.g., Donaghy and Larson, "Vision screening for amblyopia." EyeRounds.org. (Aug. 11, 2015; EyeRounds.org/tutorials/amblyopia/). The treatments can be provided daily, e.g., one, two, three, or more times daily, e.g., for at least 10, 20, 30, 40, 50, 60, or 90 minutes at a time, or less frequently, e.g., every other day, every third day, weekly, or monthly.

Figure 2:
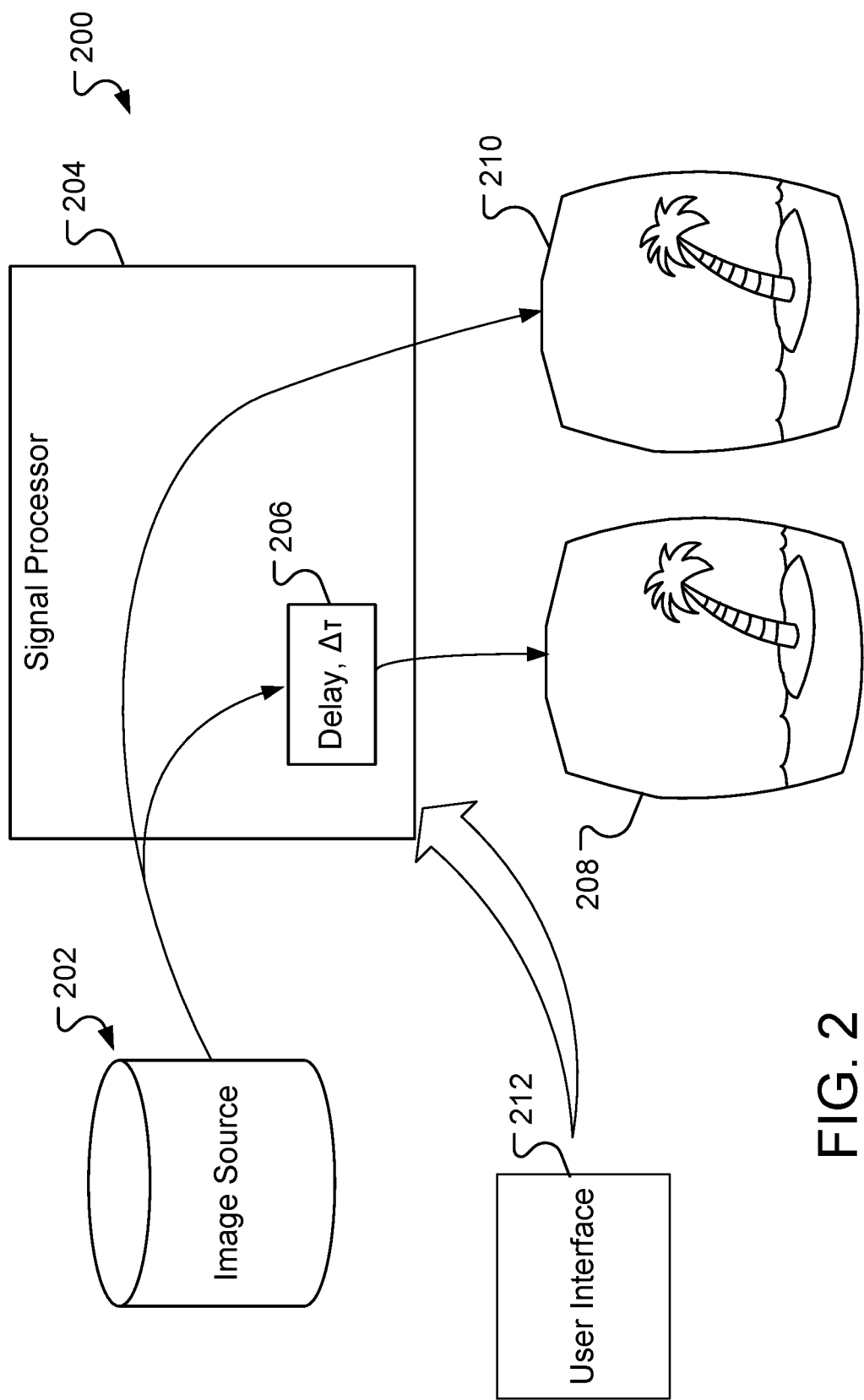
FIG. 2 illustrates an example of delaying the presentation of an image to the preferred eye.

FIG. 2 illustrates an example of delaying the presentation of an image to the preferred eye. In patients with amblyopia, a system 200 can present images, or subparts of an image, to each eye separately (images 208, 210) with interocular variation in the phase/timing of the visual stimulus presentation. The system 200 may obtain an image from an entire image source 202. A signal processor 204 may delay 206 the delivery of the image, or parts of this image, to a screen 208 associated with the preferred eye and may allow the direct delivery of the image, or parts of this image, to a screen 210 associated with the affected eye. The delay to offset ($\Delta\tau$) 206 may range from 1 ms to 1000 ms but may more commonly be in the range of 5-40 ms at 5 ms intervals. The offset may be reversed such that the image(s), or parts of the image(s), is presented to the affected/amblyopic eye after it is presented to the preferred/fellow eye.

In some implementations, a subpart of an image is delayed to the eye. In some implementations, the delayed portion of the image may be related to the content of the image. For example, if an image included mountains in the background and a house in the foreground, only the portion of the image that includes the house may be delayed. In other implementations, a geometric portion of the image that is unrelated to the content of the image may be delayed (for example, a square portion, a circular portion, the left side, the right side, etc.)

In some implementations, the delay offset 206 may be determined, at least in part, by the refresh rate of the screen (or other presentation medium). For example, many screens and presentations devices have specific refresh rates. The refresh rate is the number of frames that can be presented in a second. A refresh rate of 60 Hz corresponds to the ability to present 60 frames per second (or 1 frame every 16.67 ms), 120 Hz corresponds to 120 frames per second (or 1 frames every 8.33 ms), 240 Hz corresponds to 240 frames per second (or 1 frame every 4.167 ms), etc.

In some implementations, the delay offset may be variable and adjusted based on testing of the user's visual system to determine the inherent lag between simultaneously originating singles from the deprived and fellow eyes as they travel from the retina to the primary visual cortex. The inherent lag may be ascertained by, for example, monitoring the P1, also known as P100, event related brain potential components by using, for example, electroencephalography (EEG). The inherent lag may also be determined using other methods. For example, in some implementations, the inherent lag may be determined by testing multiple delay times and then carrying out measurements at each level to determine when there is the desired response (improved binocularity).

In particular, EEG can be used to record the responses in the brain that arrived after a stimulus is presented to the user's eyes. The lag can be measured from the time the stimulus is delivered until the P100 response is detected. In some implementations, this lag corresponds to the lag applied to the frames in the video, or the degree of contrast applied to the video. The lag may be obtained by measuring the latencies from each eye stimulated separately, and then subtracting. In some implementations both eyes may be measured simultaneously while providing inputs to each.

In some implementations, the delay offset 206 may be described in terms of frames (1 frame on a 120 Hz presentation display corresponds to an 8.33 ms delay). In some implementations, a requested delay may be specified using a user interface 212 (for example, a user may request a 5 ms delay), the signal processor may translate the delay request to the closest delay amount supported by the presentations medium's refresh rate (for example, 8.33 ms). In other implementations, the user interface 212 may limit delay options based on the specifying refresh rates supported by the presentation medium.

The system can be adapted to use any presentation medium that enables the controlled delivery of images to the preferred eye and affected eye individually. Such presentation mediums include, but are not limited to, 3D televisions (using a single screen to project separate images to each eye through various methods), virtual reality systems (including but not limited to separate display systems projected to each eye that does not incorporate the subject's surrounding visual world), and augmented reality systems (including but not limited to separate display systems projected to each eye that does integrate the subject's surrounding visual world).

Figure 3:
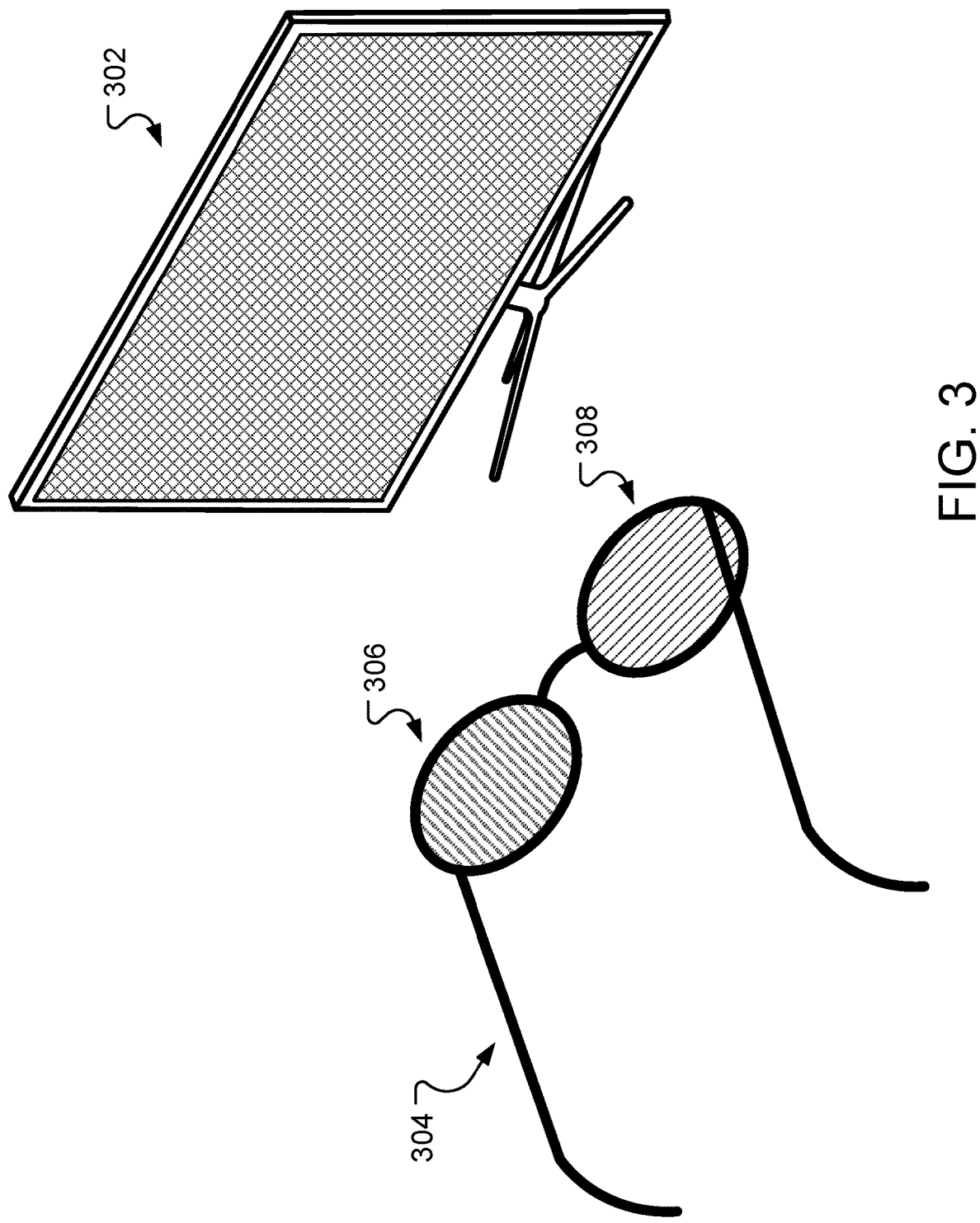
FIG. 3 illustrates an example of 3D television using glasses.

FIG. 3 illustrates an example of 3D television 302 using glasses 304. Some 3D televisions 302 present two images simultaneously on a screen (represented by the cross hatching). Special glasses 304 use various techniques to deliver separate images to each eye (represented by the vertical hashing 306 and the horizontal hashing 308).

In some implementations, a single screen system can use chromatic filters to selectively display different images to each eye. Glasses may have colored lenses, e.g. one red and one cyan, also known as anaglyph glasses. The single screen would display signals comprising each of these colors with a predefined timing offset as described above. Another approach uses polarized filters in the glasses 304. The 3D television 302 displays two images projected from the screen using differentially polarized light. The reciprocally oriented polarizing filters, so the left lens selectively filters one set of images and the right lens selectively filters a separate set of images. The single screen projects selectively filterable images with a defined timing offset as described above.

Another form of a single screen system involves active-shutter glasses, and is commonly used in readily available 3D televisions. Battery powered glasses include a shuttering system that opens and closes the left and right lenses at very high speed. At a certain moment, the left lens is "open" and viewing the left-eye image on the TV screen while the right lens is occluded. A fraction of a second later, the glasses reverse: the right lens opens, the left lens is occluded. The images projected by the screen may change or alternate according to this shutter reversal. This enables the system to send different images to the left and right eye with control over timing of visual input.

Figure 4:
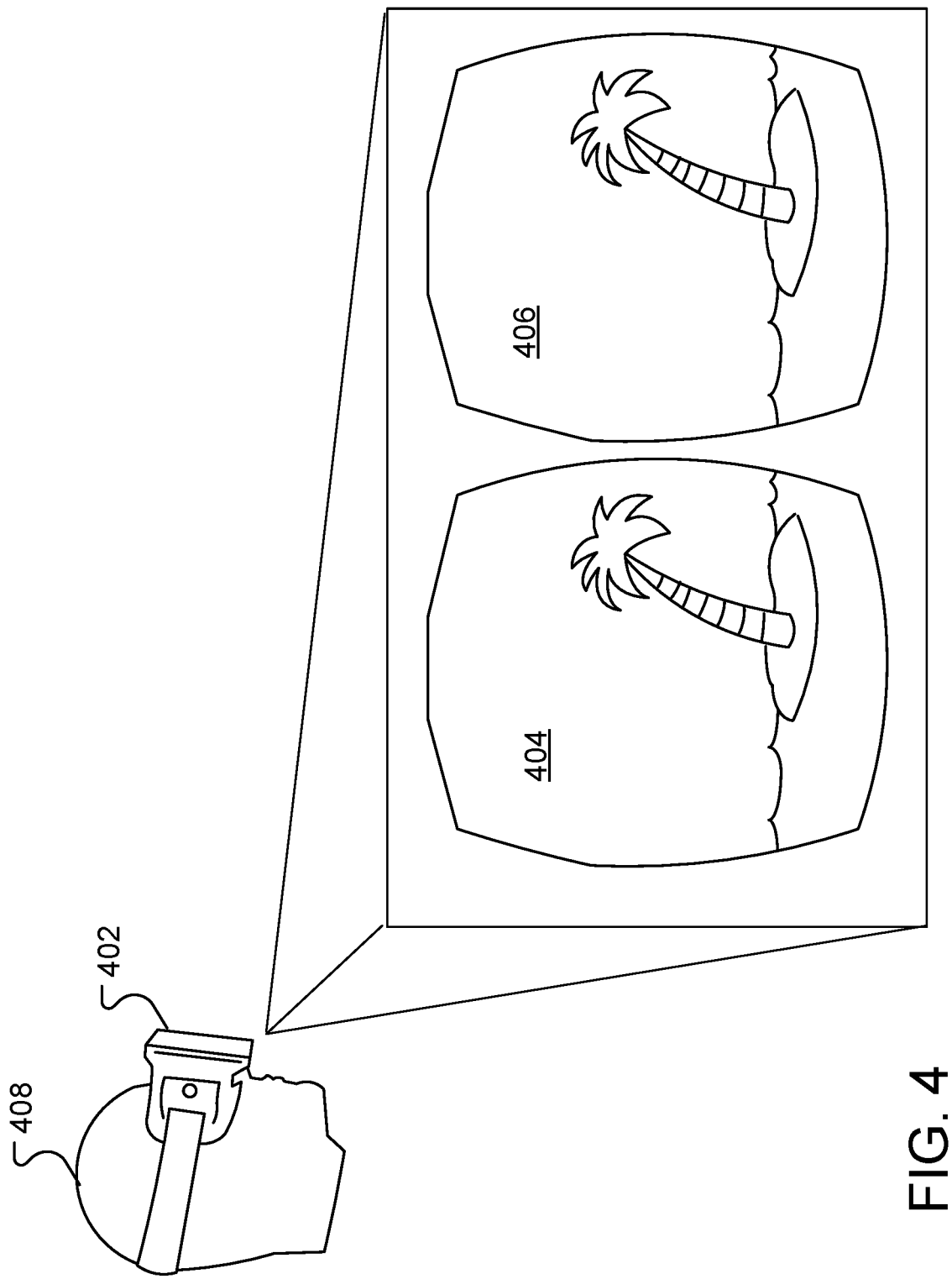
FIG. 4 illustrates an example of presenting images using a virtual reality headset.

FIG. 4 illustrates an example of presenting images using a virtual reality headset. A patient 408 wearing a virtual reality headset 402. The virtual reality headset 402 includes either one segmented screen or two separate screens. The screens present one image 404 to the left eye and another image to the right eye. Often times, the images are slightly different to present the perception of depth (i.e. a stereoscopic image). Though, it is also the case that images can be presented to each eye such that there is not any perceived depth to the image.

In order to treat amblyopia, the system may interact with, for example, a device single or two-screen system to present two separate images or sets of images to a patient. Patients with ocular misalignment can have the necessary prismatic correction overlaid to achieve binocular viewing. Alternatively, separate images or sets of images can be presented via separate displays dedicated to each eye, such as in the form of glasses or goggles with separate displays within each ocular frame (such as a virtual reality headset). The images presented can be identical/superimposed, or can differ slightly with respect to perspective/spatial relationships between objects within the image to give the impression of depth (i.e. three dimensionality). Presentation of multiple shapes at a given flicker frequency with an interocular phase shift/delay can allow for visual acuity testing.

Visual stimuli/inputs can range from simple lines/shapes to complex videos such as movies or even immersive virtual environments. Phase delay technology can be combined with interactive modules to allow for feedback from the subject, a complex example of which is an interactive video game. Such an interface can be used to provide a readout for visual perception and monitor improvement and adherence to a given treatment regimen. Presentation of multiple shapes at a given flicker frequency and interocular phase shift can allow for testing of multiple forms of visual acuity, including but not limited to spatial acuity, temporal, spectral and stereoscopic acuities (which are differentially affected in amblyopia). Also, phase delay technology can also be combined with any form of digital media or arrangement of rendered pixels that is presentable using one of the herein described methods (e.g. virtual reality, 3D televisions, augmented reality, etc.), such as still images, TV/Movie content, computer operating systems, etc.

Concomitant VEP recordings can be used in conjunction with phase delay technology. The VEP recording, and interocular delay measured, can drive the $\Delta\tau$ offset in the visual input (feedback loop) to achieve a desired target for temporal integration. The present methods can also be used in conjunction with other treatment methods; for example, contrast can be altered in one or both eyes to balance the functional utility of one eye and/or to reduce suppression while phase delay is in place. Phase delay technology can be combined with virtual or augmented reality technologies as described above to immerse the patient in their visual experience. Phase delay can also be combined with other forms of virtual or augmented reality systems which use other sensory modalities, such as sound and tactile feedback. See, e.g., Hess and Thompson, 2015, for a description of other treatment methods that can be combined with the present methods.

Figure 5:
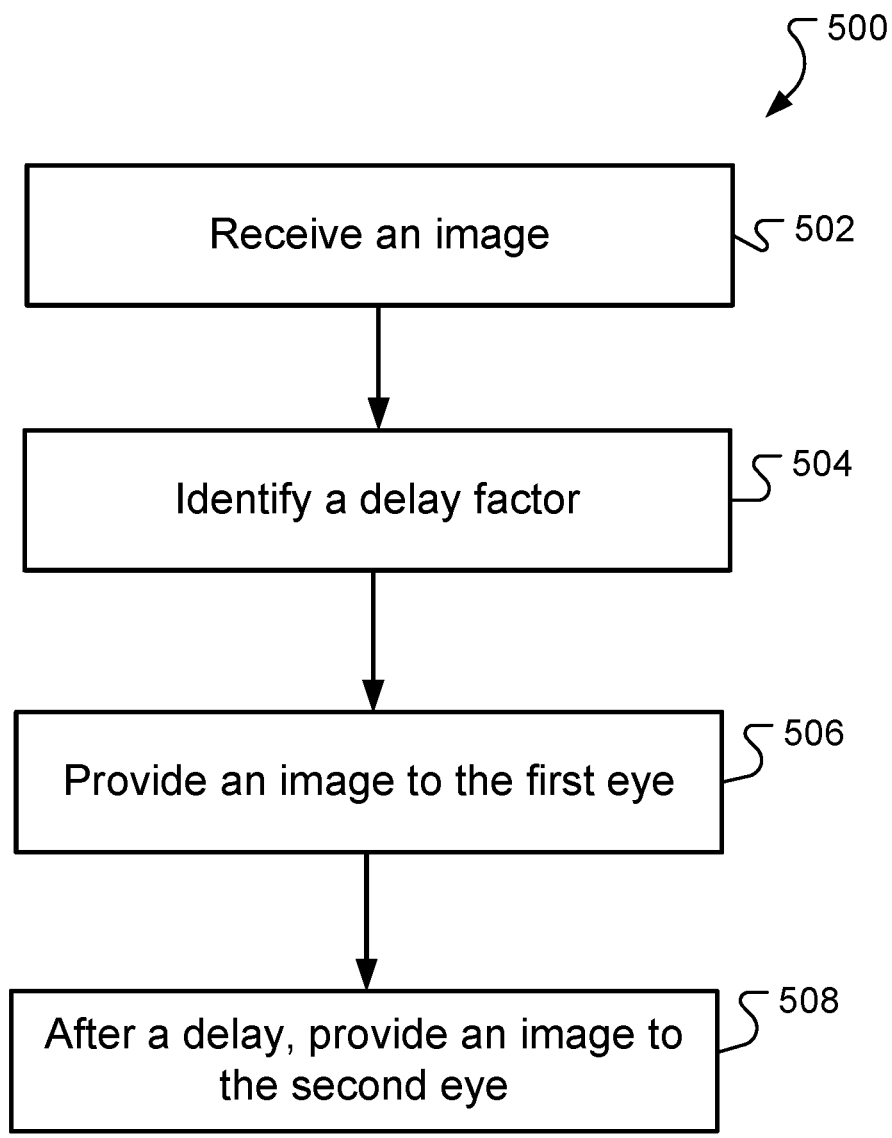
FIG. 5 is a flowchart of an example process for treating Amblyopia.

FIG. 5 is a flowchart of an example process 500 for treating amblyopia. The process can be performed using a display system capable of delivering a first image to a first eye of a patient and a second image to a second eye of a patient (such as a 3D television or virtual reality headset) and a controller capable of delaying the delivery of the second image to the second eye of the patent.

The process 500 receives 502 an image. The image may be received from a data store, may be part of a movie, may be generated as part of a video game, or may be received from any other source. In some implementations, the process may receive an image for delivery to the preferred eye and a different image for delivery to the affected eye. In some implementations, the same image is delivered to the preferred eye and the affected eye.

The process 500 identifies a delay factor 502. The delay factor may indicate a number of frames, refreshes, or milliseconds to delay the presentation of the image to the preferred eye. The delay factor identified through visual acuity or electrophysiologic testing (VEP/EEG) will provide guidance in determining the $\Delta\tau$ offset, but the delay factor identified 504 may or may not equal the $\Delta\tau$ offset (508). Alternatively, in an interactive model, behavioral (i.e. psychophysical) responses of the subject may be used to determine the perception of an interocular timing delay. Those responses, in turn, could be used to influence the delay factor. The delay factor may or may not change over the course of treatment or implementation of this system as guided by measures obtained through methods including but not limited to electrophysiologic and psychophysical/behavioral means.

The process 500 provides 506 the image to the affected eye.

After a delay determined by the delay factor, the process 500 provides 508 the image to the preferred eye. In some implementations, this process may be reversed such that the first image is presented to the preferred eye and subsequently to the affected eye with a delay as determined by the delay factor.

Figure 6A:
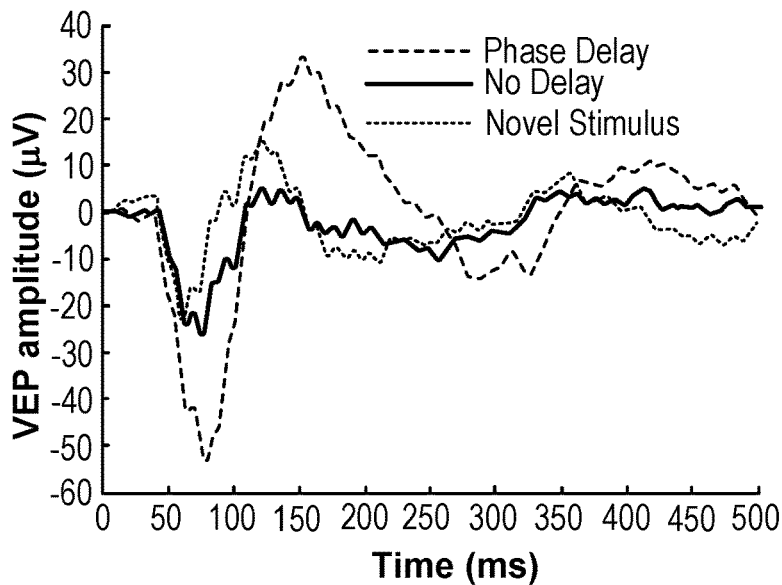
FIG. 6A-C are charts illustrating the experimental effects of introducing a delay factor in delivering images.
Figure 6B:
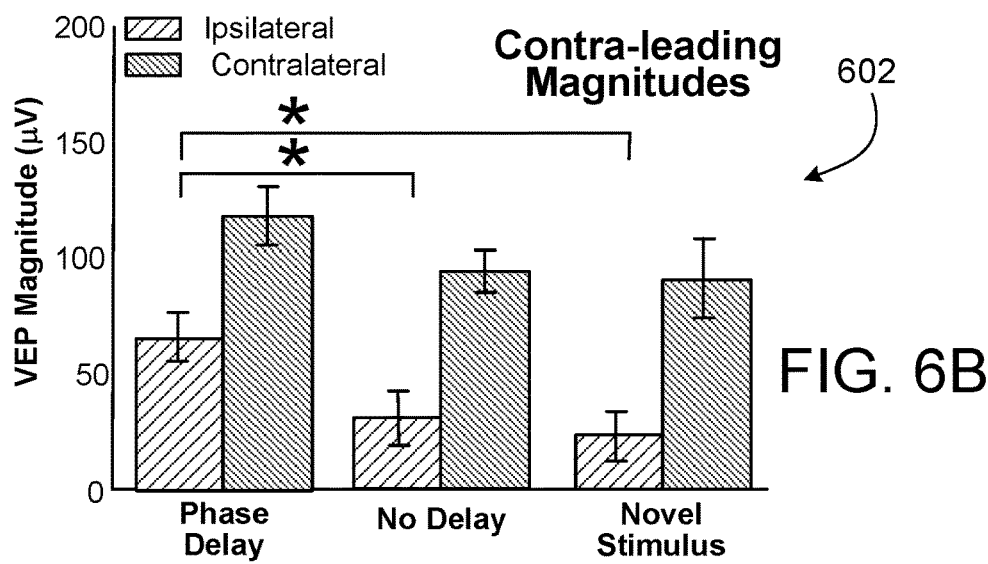
Figure 6C:
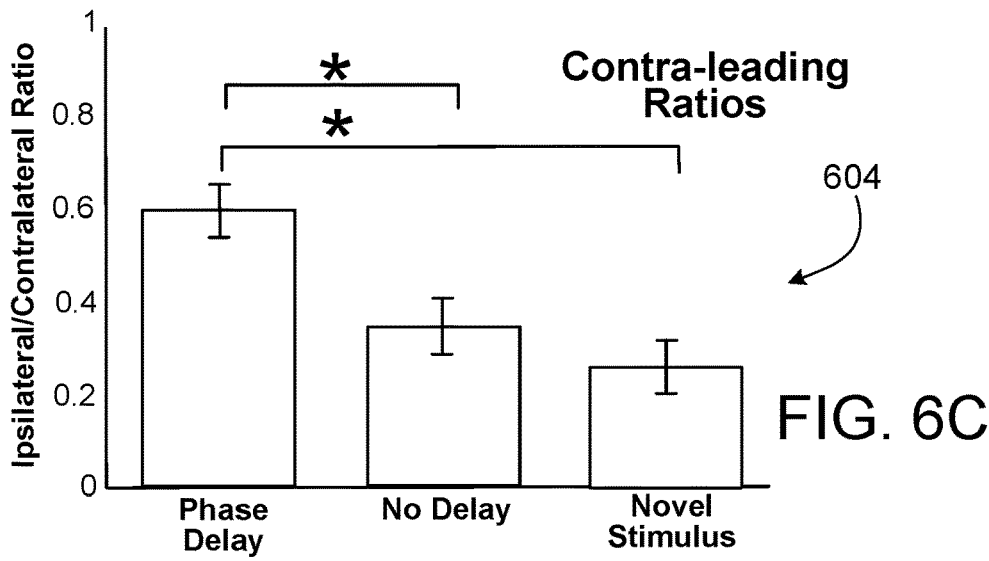

FIG. 6A-C are charts illustrating the experimental effects of introducing a delay factor in delivering images in a mouse model. These experiments were performed with the goal of enhancing the effect of treatment for neurologic conditions whose pathologies may be addressed through synaptic plasticity. These experiments employ one form of synaptic plasticity is demonstrated through binocular visually evoked potentials (VEPs) which potentiate when the same visual stimulus orientation is presented repeatedly over days in mice (training). The potentiation is specific to the stimulus orientation that was repeatedly shown to the animal such that an orthogonally oriented sinusoidal stimulus is shown after training produces a VEP amplitude that is at the original baseline level. In this sense this potentiation is stimulus-selective and specific, and thus this phenomenon has been termed stimulus-selective response plasticity (SRP). In order to evaluate the effect of offsetting the timing of stimuli on synaptic plasticity, we used the SRP model to test the effect of an interocular stimulus offset on ocular dominance plasticity in mice.

A single screen was used to present exclusively polarized stimuli to the animal, and the stimuli were selectively filtered to each eye with a controlled offset in head-fixed mice. The stimulus consisted of a sinusoidal, 100% contrast grating at 0.05 cycles per degree in a fixed orientation. The tests included monocular and binocular testing at using stimuli of 4 different sinusoidal orientations: X+30 degrees, X+60 degrees, X+90 degrees, and X+120 degrees. Other ranges can also be used. Local field potentials (VEPs) were recorded through implanted electrodes in the striate cortex (V1 region). As in normal in prey animals, the VEP to magnitude recorded in one primary visual cortical hemisphere is consistently smaller for the ipsilateral eye than that for the contralateral eye (relative to the cortical hemisphere being recorded) across all tests. The stimulus offset was such that the visual stimulus was presented to the eye contralateral to the recording electrode 16 ms before the same stimulus was presented to the ipsilateral eye. The visual stimulus was shown to the animal for 15 minutes at a rate of 0.5 Hz daily for 5 days. Two orthogonal orientations were run in parallel, one with an interocular stimulus offset ("Phase Delay") and the other with no offset (No Delay). The final VEP magnitudes were compared to that produced by a third, novel stimulus orientation ("Novel Stimulus"). Graph 600 shows the VEP amplitude to time, in milliseconds. The bar graph 602 illustrates the VEP magnitude for the ipsilateral and contralateral visual stimuli, with respect to the side of visual cortex from which recordings were obtained. These conditions were compared to one another for the ipsilateral eye (A) as well as the contralateral eye (B). The magnitude of the ipsilateral VEP was significantly larger for the phase delay condition compared to the no delay and novel stimulus conditions, which were not different from one another. These results were consistently seen across a total of 3 adult animals and 3 juvenile animals tested in the same way. There were no differences seen across conditions for the contralateral eye. The bar graph 604 illustrates the ipsilateral/contralateral VEP signal ratio. Taking the ispilateral:contralateral VEP ratio, the same potentiating effect of phase delay was appreciated above the no delay and novel stimulus conditions (C). No SRP was appreciated in the no delay condition likely because monocular responses were tested in this condition. Similar results were seen across 2 animals in which the stimulus was presented to the ipsilateral eye and subsequently to the contralateral eye with the same 16 ms delay, that is, a potentiation was seen in the VEP signal corresponding to the ipsilateral eye (2 animals, data not shown). These data demonstrate that an interocular visual stimulus timing offset (i.e. phase delay) is sufficient to induce neural and/or synaptic plasticity in the mammalian visual cortex.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs (i.e., one or more modules of computer program instructions, encoded on computer storage mediums for execution by, or to control the operation of, data processing apparatus). A computer storage medium can be, or be included in, a computer-readable storage device, a computer-readable storage substrate, a random or serial access memory array or device, or a combination of one or more of them. The computer storage medium can also be, or be included in, one or more separate physical components or media (e.g., multiple CDs, disks, or other storage devices). The computer storage medium can be non-transitory.

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example, a programmable processor, a computer, a system on a chip, or multiple ones, or combinations, of the foregoing. The apparatus can include special purpose logic circuitry (e.g., an FPGA (field programmable gate array) or an ASIC (application-specific integrated circuit)). The apparatus can also include, in addition to hardware, code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural or object-oriented or functional languages, and it can be deployed in any form, including as a stand-alone program or as a module, component, subroutine, service, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry (e.g., an FPGA (field programmable gate array) or an ASIC (application-specific integrated circuit)).

Processors suitable for the execution of a computer program include, by way of example, both general and special purpose microprocessors, and any one or more processors of any kind of digital, analog or quantum computer. Generally, a processor can receive instructions and data from a read-only memory or a random access memory or both. The essential elements of a computer are a processor for performing actions in accordance with instructions and one or more memory devices for storing instructions and data. Generally, a computer can also include, or be operatively coupled to receive, data from or transfer data to, or both, one or more mass storage devices for storing data (e.g., electronic, magnetic, magneto-optical disks, or optical disks), however, a computer need not have such devices. Moreover, a computer can be embedded in another device (e.g., a mobile telephone, a personal digital assistant (PDA), a mobile audio or video player, a game console, a GPS receiver, or a portable storage device (e.g., a universal serial bus (USB) flash drive)), to name just a few. Devices suitable for storing computer program instructions and data include all forms of non-volatile memory, media and memory devices, including by way of example semiconductor memory devices (e.g., EPROM, EEPROM, and flash memory devices), magnetic disks (e.g., internal hard disks or removable disks), magneto-optical disks, and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback) and input from the user can be received in any form, including acoustic, speech, or tactile input. In addition, a computer can interact with a user by sending documents to and receiving documents from a device that is used by the user (for example, by sending web pages to a web browser on a user's user device in response to requests received from the web browser).

Embodiments of the subject matter described in this specification can be implemented in a computing system that includes a back-end component (e.g., as a data server), a middleware component (e.g., an application server), or a front-end component (e.g., a user computer having a graphical user interface or a Web browser through which a user can interact with an implementation of the subject matter described in this specification), or any combination of one or more such back-end, middleware, or front-end components. The components of the system can be interconnected by any form or medium of digital or optical data communication (e.g., a communication network). Examples of communication networks include a local area network ("LAN") and a wide area network ("WAN"), an inter-network (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can, in some cases, be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method comprising:
receiving, at a controller comprising one or more processing devices, a first image and a second image;
identifying, by the controller, a delay factor associated with the second image;
presenting, by the controller, the first image on a portion of a display device visible to the first eye of a subject;
delivering, by the controller in accordance with the delay factor, the second image to the second eye of the subject, wherein at least a portion of the second image is delivered 1-1000 msec before or after the first image, the second image being visible to the second eye concurrently with the first image being visible to the first eye,
wherein a contrast of the second image is altered such that the contrast of the second image is different from a contrast of the first image, and
wherein the delay factor is identified based on measuring one or more parameters at each of multiple candidate delay factors.

2. The method of claim 1, wherein the first eye or the second eye is amblyopic.

3. The method of claim 1, wherein the display device comprises a single display, and the first image and the second image are presented through the single display and selectively filtered to each eye.

4. The method of claim 3, wherein the single display uses polarization to selectively deliver the first image and the second image, or chromatic filters to selectively deliver the first image and the second image.

5. The method of claim 1, wherein the display device comprises two separate displays, and the first image and the second image are presented through the separate displays.

6. The method of claim 1, wherein the first image and the second image are part of a virtual reality experience or part of an augmented reality experience.

7. The method of claim 1, wherein the one or more parameters comprise an electrophysiologic metric measured from visually evoked potential (VEP).

8. The method of claim 1, wherein the delay factor is determined at least in part using at least one of at least one of eye tracking technologies, game-based tests of binocularity or inter-ocular suppression.

9. The method of claim 1, wherein the delay factor is determined at least in part through testing a plurality of delay times, each delay time measured to determine a corresponding response and the delay factor is selected from the plurality of delay times based on measured improvements to binocularity.

10. The method of claim 1, wherein delivering at least a portion of the second image 1-1000 msec before or after the first image comprises delaying delivery of only a subpart of the second image.

11. The method of claim 1, wherein the display device comprises a single split display presented or projected to each eye, and the first image and the second image are presented through the single split display.

12. The method of claim 1, wherein the one or more parameters comprise an electrophysiologic metric measured from electroencephalography (EEG).

* * * * *

UNITED STATES PATENT AND TRADEMARK OFFICE
CERTIFICATE OF CORRECTION

| | |
|---|---|
| PATENT NO. | : 11,826,098 B2 |
| APPLICATION NO. | : 16/345632 |
| DATED | : November 28, 2023 |
| INVENTOR(S) | : Eric Gaier, Dean Travers and Scott Xiao |

It is certified that error appears in the above-identified patent and that said Letters Patent is hereby corrected as shown below:

On the Title Page

Column 2 item [57], Line 3, before "delivering" delete "in"

Column 2 item [57], Line 5, before "capable" delete "in"

Column 2 item [57], Line 6, delete "patent." and insert -- patient. --

Signed and Sealed this
Eighteenth Day of June, 2024

Katherine Kelly Vidal
*Director of the United States Patent and Trademark Office*